(12) United States Patent
Chan et al.

(10) Patent No.: US 12,073,538 B2
(45) Date of Patent: Aug. 27, 2024

(54) NEURAL NETWORK FOR IMPROVED PERFORMANCE OF MEDICAL IMAGING SYSTEMS

(71) Applicant: CANON MEDICAL SYSTEMS CORPORATION, Otawara (JP)

(72) Inventors: Chung Chan, Vernon Hills, IL (US); Li Yang, Vernon Hills, IL (US); Wenyuan Qi, Vernon Hills, IL (US); Evren Asma, Vernon Hills, IL (US); Jeffrey Kolthammer, Vernon Hills, IL (US); Yi Qiang, Vernon Hills, IL (US)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 287 days.

(21) Appl. No.: 17/225,672

(22) Filed: Apr. 8, 2021

(65) Prior Publication Data
US 2022/0327665 A1 Oct. 13, 2022

(51) Int. Cl.
*G06T 5/70* (2024.01)
*G06N 3/084* (2023.01)
*G06T 7/00* (2017.01)

(52) U.S. Cl.
CPC ............... *G06T 5/70* (2024.01); *G06N 3/084* (2013.01); *G06T 7/0012* (2013.01); *G06T 2207/20081* (2013.01); *G06T 2207/20084* (2013.01)

(58) Field of Classification Search
CPC .. G06T 5/00; G06T 5/002; G06T 7/00; G06T 7/0012; G06T 2207/20081;
(Continued)

(56) References Cited

U.S. PATENT DOCUMENTS 10,949,951 B2 * 3/2021 Tang ...................... G16H 30/20
11,361,431 B2 * 6/2022 Zaharchuk ............ G06T 7/0012
(Continued)

OTHER PUBLICATIONS

Schuon, Sebastian, et al. "High-quality scanning using time-of-flight depth superresolution." 2008 IEEE Computer Society Conference on Computer Vision and Pattern Recognition Workshops. IEEE, 2008. (Year: 2008) (Year: 2008).*
(Continued)

*Primary Examiner* — Edward F Urban
*Assistant Examiner* — Benedict E Lee
(74) *Attorney, Agent, or Firm* — Oblon, McClelland, Maier & Neustadt, L.L.P.

(57) ABSTRACT

Existing, low quality images can be restored using reconstruction or a combination of post-reconstruction techniques to generate a real patient phantom. The real patient phantom (RPP) can then be simulated in Monte Carlo simulations of a higher performance system and a lower performance system. Alternatively, the RPP can be simulated in the higher performance system, and a real scan can be performed by an existing, lower performance system. The higher performance system can be differentiated from the lower performance system in a variety of ways, including a higher resolution time of flight measurement capability, a greater sensitivity, smaller detector crystals, or less scattering. A neural network can be trained using the images produce by the higher performance system as the target, and the images produced by the lower performance system as the input. After training, the trained neural network can be used to output input images taken in a lower performance system with higher performance system characteristics.

18 Claims, 7 Drawing Sheets

(58) Field of Classification Search
CPC .......... G06T 2207/20084; G06T 11/00; G06T 11/006; G06T 2207/10072; G06T 2207/10132; G06T 2207/30004; G06N 3/084; A61B 6/03; A61B 6/037
See application file for complete search history.

(56) References Cited

U.S. PATENT DOCUMENTS

| | | | |
|---|---|---|---|
| 11,576,628 B2* | 2/2023 | Kaplan | G06N 3/084 |
| 11,610,346 B2* | 3/2023 | Atria | G06T 11/006 |
| 2006/0153339 A1* | 7/2006 | Ueno | G01T 1/1615 378/189 |
| 2009/0096787 A1* | 4/2009 | Masumoto | G06T 7/0012 382/131 |
| 2010/0074487 A1* | 3/2010 | Miyamoto | G06T 7/32 382/128 |
| 2013/0135287 A1* | 5/2013 | McCabe | A61B 6/5247 345/419 |
| 2017/0071562 A1 | 3/2017 | Suzuki | |
| 2017/0164910 A1* | 6/2017 | Cao | A61B 6/4275 |
| 2018/0018757 A1 | 1/2018 | Suzuki | |
| 2018/0211419 A1* | 7/2018 | Zhu | G06T 7/337 |
| 2019/0050973 A1* | 2/2019 | Bernal | H04N 7/181 |
| 2019/0101655 A1* | 4/2019 | Wang | G01R 33/28 |
| 2019/0365341 A1* | 12/2019 | Chan | G06T 7/0012 |
| 2020/0005495 A1 | 1/2020 | Teshigawara et al. | |
| 2020/0196973 A1 | 6/2020 | Zhou et al. | |
| 2020/0311914 A1 | 10/2020 | Zaharchuk et al. | |
| 2020/0342637 A1 | 10/2020 | Zhang et al. | |
| 2021/0074036 A1* | 3/2021 | Fuchs | G06T 11/006 |
| 2021/0174496 A1* | 6/2021 | Annangi | A61B 8/52 |
| 2021/0319557 A1* | 10/2021 | Gooding | A61B 6/5217 |
| 2022/0036514 A1* | 2/2022 | Niu | G06T 5/002 |
| 2023/0022206 A1* | 1/2023 | Wang | G16H 50/30 |
| 2023/0070249 A1* | 3/2023 | Shi | G06T 7/62 |

OTHER PUBLICATIONS

Wollenweber, Scott D., and Brad J. Kemp. "rod phantom analysis for comparison of PET detector sampling and reconstruction methods." Medical physics 43.11 (2016): 6175-6185. (Year: 2016) (Year: 2016).*

Schuon, Sebastian, et al. "High-quality scanning using time-of-flight depth superresolution." 2008 IEEE Computer Society Conference on Computer Vision and Pattern Recognition Workshops. IEEE, 2008. (Year: 2008).*

Wollenweber, Scott D., and Brad J. Kemp. "rod phantom analysis for comparison of PET detector sampling and reconstruction methods." Medical physics 43.11 (2016): 6175-6185. (Year: 2016).*

Peter, Jörg, Martin P. Tornai, and Ronald J. Jaszczak. "Analytical versus voxelized phantom representation for Monte Carlo simulation in radiological imaging." IEEE transactions on medical imaging 19.5 (2000): 556-564. (Year: 2000).*

* cited by examiner

NEURAL NETWORK FOR IMPROVED PERFORMANCE OF MEDICAL IMAGING SYSTEMS

FIELD OF THE INVENTION

The present disclosure is related to using a neural network to improve image quality in medical imaging systems.

BACKGROUND

The quality of medical images are often limited by many confounding factors, including radiation exposure, imaging time, physics, and cost of hardware. For a medical imaging scanner (e.g., PET, SPECT, CT), one way to acquire a higher quality image, having high contrast and low noise, is to increase radiation dosage or the imaging time, but this can be very harmful to a patient's health. On the other hand, increasing imaging time reduces patient throughput. In other words, there is a tradeoff between image quality and dosage level. Therefore, in PET/SPECT, clinical protocols typically have limited acquisition durations, and there is a limited amount of radiotracer that can be injected into a patient.

Alternatively, using medical imaging scanners with smaller crystals sizes, higher sensitivity, less scatter, faster time of flight (TOF) resolution, or any combination thereof can improve image quality without having to increase radiation dosage or imaging time, but this comes at the expense of increased hardware costs and engineering efforts. Therefore, in light of the above mentioned problems, there exists a need to be able to cost-effectively produce high quality medical images without increasing risk to patients.

SUMMARY

The present disclosure presents a medical image processing apparatus comprising: processing circuitry configured to, obtain first radiation data from the medical image processing apparatus; and generate second radiation data by inputting the first radiation data into a trained neural network, wherein the trained neural network is a neural network trained by obtaining a higher performance system dataset by simulating obtaining by a higher performance system third radiation data, obtaining a lower performance system dataset, and training the neural network by using the higher performance system dataset as a target for the neural network, and the lower performance system dataset as an input for the neural network.

In one exemplary aspect, the third radiation data is generated by reconstructing fourth radiation data using at least one of denoising and partial volume correction techniques.

In one exemplary aspect, the higher performance system has a higher resolution time of flight measurement capability than the lower performance system.

In one exemplary aspect, the higher performance system has a greater sensitivity than the lower performance system.

In one exemplary aspect, the higher performance system has smaller detector crystals than the lower performance system.

In one exemplary aspect, the higher performance system has less scattering than the lower performance system.

In one exemplary aspect, the first, second, third, and fourth radiation data are at least one of PET data and CT data.

In one exemplary aspect, the first, second, third, and fourth radiation data are gated PET data.

In one exemplary aspect, the lower performance system dataset is obtained from at least one of (a) a real scan by the medical image processing apparatus and (b) simulating obtaining by a lower performance system the third radiation data.

In one exemplary aspect, the neural network is a deep convolution neural network.

The present disclosure also presents a method comprising: obtaining first radiation data from a medical image processing apparatus; and generating second radiation data by inputting the first radiation data into a trained neural network, wherein the trained neural network is a neural network trained by obtaining a higher performance system dataset by simulating obtaining by a higher performance system third radiation data, obtaining a lower performance system dataset, and training the neural network by using the higher performance system dataset as a target for the neural network, and the lower performance system dataset as an input for the neural network.

In one exemplary aspect, the third radiation data is generated by reconstructing fourth radiation data using at least one of denoising and partial volume correction techniques.

In one exemplary aspect, the higher performance system has a higher resolution time of flight measurement capability than the lower performance system.

In one exemplary aspect, the higher performance system has a greater sensitivity than the lower performance system.

In one exemplary aspect, the higher performance system has smaller detector crystals than the lower performance system.

In one exemplary aspect, the higher performance system has less scattering than the lower performance system.

In one exemplary aspect, the first, second, third, and fourth radiation data are at least one of PET data and CT data.

In one exemplary aspect, the lower performance system dataset is obtained from at least one of (a) a real scan by the medical image processing apparatus and (b) simulating obtaining by a lower performance system the third radiation data.

In one exemplary aspect, the neural network is a deep convolution neural network.

The present disclosure also presents a non-transitory computer-readable storage medium storing computer-readable instructions that, when executed by a computer, cause the computer to perform a method comprising: receiving first radiation data from a medical image processing apparatus; and generating second radiation data by inputting the first radiation data into a trained neural network, wherein the trained neural network is a neural network trained by obtaining a higher performance system dataset by simulating obtaining by a higher performance system third radiation data, obtaining a lower performance system dataset, and training the neural network by using the higher performance system dataset as a target for the neural network, and the lower performance system dataset as an input for the neural network.

DETAILED DESCRIPTION

Figure 1:
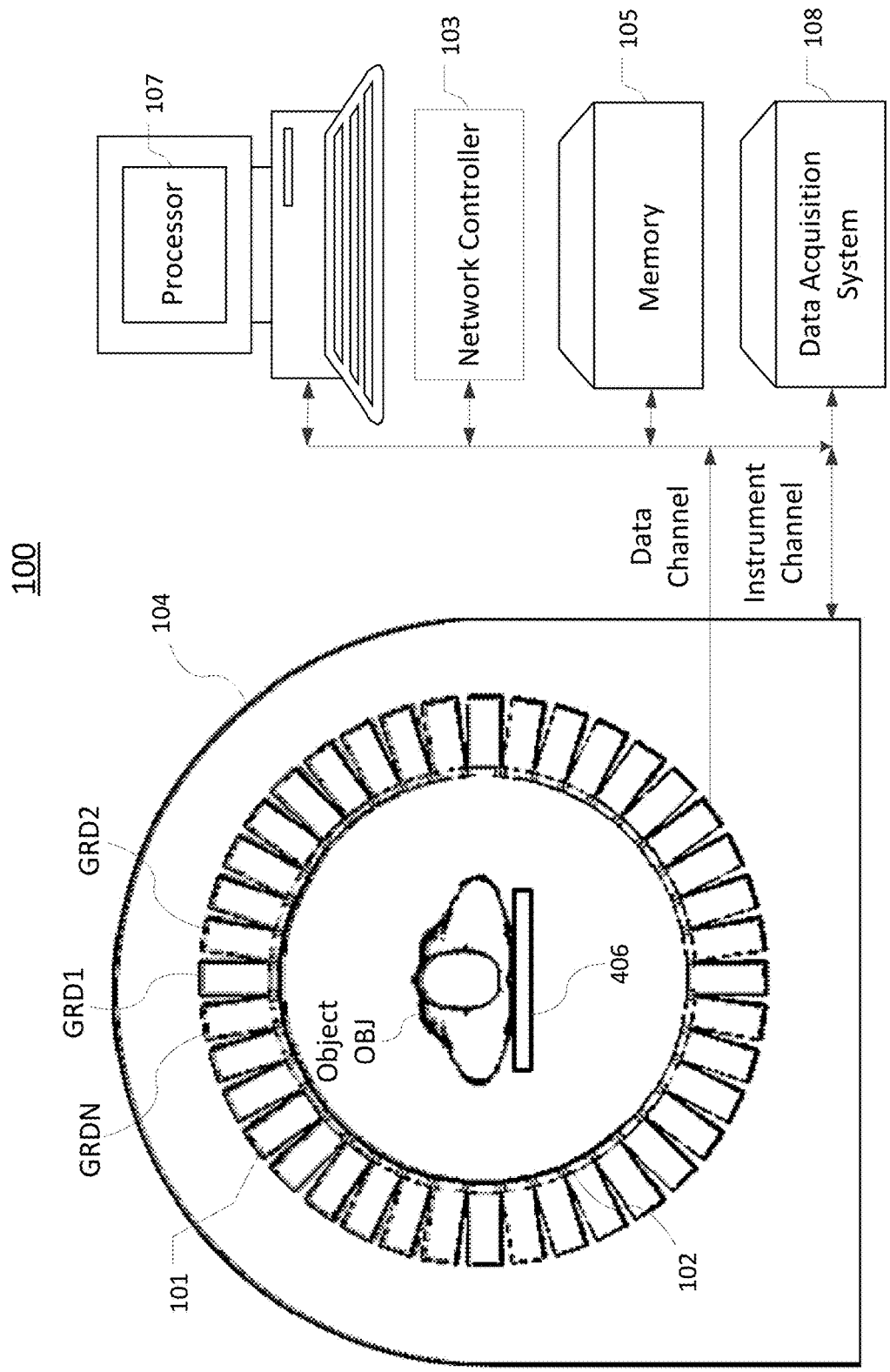
FIG. 1 is a schematic of a PET scanner and associated hardware, according to one exemplary aspect.

The following disclosure provides many different embodiments, or examples, for implementing different features of the provided subject matter. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed.

The order of discussion of the different steps as described herein has been presented for the sake of clarity. In general, these steps can be performed in any suitable order. Additionally, although each of the different features, techniques, configurations, etc. herein may be discussed in different places of this disclosure, it is intended that each of the concepts can be executed independently of each other or in combination with each other. Accordingly, the present invention can be embodied and viewed in many different ways. This disclosure describes a positron emission tomography (PET) detector to illustrate the various embodiments, but these concepts can be applied to similar systems, including single-photon emission computed tomography (SPECT) systems, magnetic resonance imaging (MRI) systems, ultrasound systems, computed tomography (CT) systems, and PET-CT systems. The disclosure describes using radiation data, which can include images. Further, as used herein, the words "a", "an" and the like generally carry a meaning of "one or more", unless stated otherwise.

This disclosure is directed to generating and utilizing a trained neural network to improve denoising performance of a system. In one embodiment, the neural network is a deep convolution neural network (DCNN). To train the DCNN, a low quality, existing image, such as a PET image, can be transformed using partial volume correction or denoising techniques to create a piece-wise, smooth image with sharp organ or lesion boundaries (while maintaining the radiotracer distribution), referred to herein as a real patient phantom (RPP). The RPP can be used as a voxelized phantom in Monte Carlo simulations for both (i) a lower performance system, and (ii) a higher performance system. The RPP can be simulated in the lower performance system to generate a lower performance system dataset, and the RPP can be simulated in the higher performance system to generate a higher performance system dataset. In another embodiment, the lower performance system dataset can be generated from a real scan by a real, existing system (instead of simulating). To train the DCNN, the lower performance dataset (obtained from a real scan or via simulating) can be used as the input, and the simulated higher performance system dataset can be used as the high quality target. After the DCNN has been trained, a real, existing system scan can be input into the DCNN to generate a predicted higher performance system scan of that input (without having to perform an actual scan in a higher performance system). The result is an image of higher quality that exceeds beyond the physical limitations of the real, existing system used to gather the initial image or radiation data.

Acquiring high quality training datasets is a major hurdle in training a DCNN to improve medical image quality. The techniques disclosed herein can generate realistic, high quality training data using existing real patient datasets, which enables advantages that include: significant reduction in cost, complexity, risk, and time frame in acquiring high quality training datasets of real human subjects; more realistic patient characteristics and radiotracer distributions than a simple mathematical/numerical phantom; ability to retrospectively include unique disease patterns or specific organs that were previously acquired to augment an existing training dataset for neural network fine tuning; and enables the training of a neural network that can be applied to dynamic, respiratory and cardiac gated PET acquisitions. All of these advantages can be achieved without having to change the medical imaging scanner's hardware.

According to one exemplary embodiment, this disclosure presents a medical image processing apparatus comprising: processing circuitry configured to, obtain first radiation data from the medical image processing apparatus; and generate second radiation data by inputting the first radiation data into a trained neural network, wherein the trained neural network is a neural network trained by obtaining a higher performance system dataset by simulating obtaining by a higher performance system third radiation data, obtaining a lower performance system dataset, wherein the lower performance system dataset is obtained from at least one of a real scan by the medical image processing apparatus, or by simulating obtaining by a lower performance system the third radiation data, and training the neural network by using the higher performance system dataset as a target for the neural network, and the lower performance system dataset as an input for the neural network.

According to one exemplary aspect, the third radiation data (i.e. RPP) is generated by reconstructing fourth radiation data using at least one of denoising and partial volume correction techniques. The fourth radiation data can be a pre-existing image, according to one exemplary embodiment.

According to one exemplary aspect, the lower performance system used in the simulation can be modelled after a pre-existing, real-life medical imaging processing apparatus that was used to capture the first radiation data. The higher performance system can be differentiated from the lower performance system in a myriad of different ways, including: the higher performance system has a higher resolution time of flight measurement capability than the lower performance system; the higher performance system has a greater sensitivity than the lower performance system; the higher performance system has smaller detector crystals than the lower performance system; the higher performance system has less scattering (e.g. Compton scattering) than the lower performance system; or any combination thereof.

The first, second, third, and fourth radiation data can be PET data, gated PET data, CT data, MRI data, or any other data that can be understood to work with the techniques discussed herein.

In one exemplary aspect, the neural network is a deep convolution neural network. In other embodiments, the neural network can be a different type of neural network, such as an artificial neural network or a recurrent neural network.

In one exemplary embodiment, it can be appreciated that the system in the present disclosure may be implemented within a PET scanner. FIG. 1 shows a schematic view of a PET scanner system having GRDs arranged to detect gamma-rays emitted from an object OBJ (e.g., a patient). The GRDs can measure the timing, position, and energy corresponding to each gamma-ray detection. In one implementation, the gamma-ray detectors are arranged in a PET detector ring, as shown in FIG. 1. It can be appreciated that the single PET detector ring of FIG. 1 can be extrapolated to include any number of PET detector rings along an axial length of the PET scanner. The detector crystals can be scintillator crystals, which have individual scintillator elements arranged in a two-dimensional array and the scintillator elements can be any known scintillating material. The PMTs can be arranged such that light from each scintillator element is detected by multiple PMTs to enable Anger arithmetic and crystal decoding of scintillation event.

FIG. 1 shows an example of the arrangement of the PET scanner 100, in which an object OBJ (e.g., a possibly infected person) rests on a table 106 and the GRD modules GRD1 through GRDN are arranged circumferentially around the object OBJ (e.g., a patient) and the table 106. The GRDs may comprise a PET detector ring and may fixedly-connected to a circular bore 102 that is fixedly-connected to a gantry 104. The gantry 104 houses many parts of the PET scanner 100. The gantry 104 of the PET scanner 100 also includes an open aperture, defined by the cylindrical bore 102, through which the object OBJ (e.g., a patient) and the table 106 can pass, and gamma-rays emitted in opposite directions from the object OBJ (e.g., a patient) due to an annihilation event can be detected by the GRDs and timing and energy information can be used to determine coincidences for gamma-ray pairs.

In FIG. 1, circuitry and hardware is also shown for acquiring, storing, processing, and distributing gamma-ray detection data. The circuitry and hardware include a processor 107, a network controller 103, a memory 105, and a data acquisition system (DAS) 108. The PET imager also includes a data channel that routes detection measurement results from the GRDs to the DAS 108, the processor 107, the memory 105, and the network controller 103. The DAS 108 can control the acquisition, digitization, and routing of the detection data from the detectors. In one implementation, the DAS 108 controls the movement of the table 106. The processor 107 performs functions including pre-reconstruction processing of the detection data, image reconstruction, and post-reconstruction processing of the image data. The processor 107 can be configured to perform any of the methods or workflows that discussed herein, such as method 200, method 300, or workflow 400 (discussed further below).

Figure 2:
FIG. 2 is a method for using a trained neural network to generate second radiation data that is of higher quality than an input, first radiation data, according to one exemplary aspect.

It can be appreciated that the above mentioned system can also be viewed as a method. FIG. 2 outlines a method 200 for utilizing a trained DCNN to take an existing image, such as one created by PET scanner 100, and improve the image beyond the existing PET scanner's 100 physical limitations.

In S201, first radiation data is obtained. In one embodiment, this radiation data is a constructed image of an object OBJ captured by the PET scanner 100. The image can be constructed using a back-projection method, filtered back-projection method, Fourier-transform-based image reconstruction method, iterative image reconstruction method, matrix-inversion image reconstruction method, statistical image reconstruction method, list-mode method, or other reconstruction method as would be understood by a person of ordinary skill in the art. The quality of this image is limited by the physical constraints of the PET scanner 100 used to capture and create the image. Examples of physical constraints can include crystal size, axial field of vision (FOV), time of flight resolution, and scattering.

In S202, this first radiation data is input into a trained DCNN. In one embodiment, the trained DCNN is configured into the processor 107. This DCNN has been trained to improve the quality of the first radiation data beyond the PET scanner's 100 physical constraints.

In S203, the trained neural network generates second radiation data. The second radiation data can be a new and improved, denoised version of the first radiation data. The second radiation data has improved the first radiation data beyond the physical limitations of the PET scanner 100 used to capture the first radiation data in at least one aspect. Examples of improvements can include a higher resolution time of flight (TOF) measurement capability, increased sensitivity, higher resolution (e.g. smaller crystals), and improved scatter correction. In other words, the second radiation data is a predicted dataset of the first radiation data had the first radiation data been obtained in a higher performance system. Further, this second radiation data can be post-processed and displayed to a user.

As an example, if a time of flight resolution of 800 picoseconds (ps) was used in S201 for creating a first image of an object OBJ by the PET scanner 100, the trained DCNN can generate an improved image in S203 as if the object OBJ was captured in a system with a higher resolution (e.g., 250 ps) time of flight time of flight measurement capability.

Figure 3:
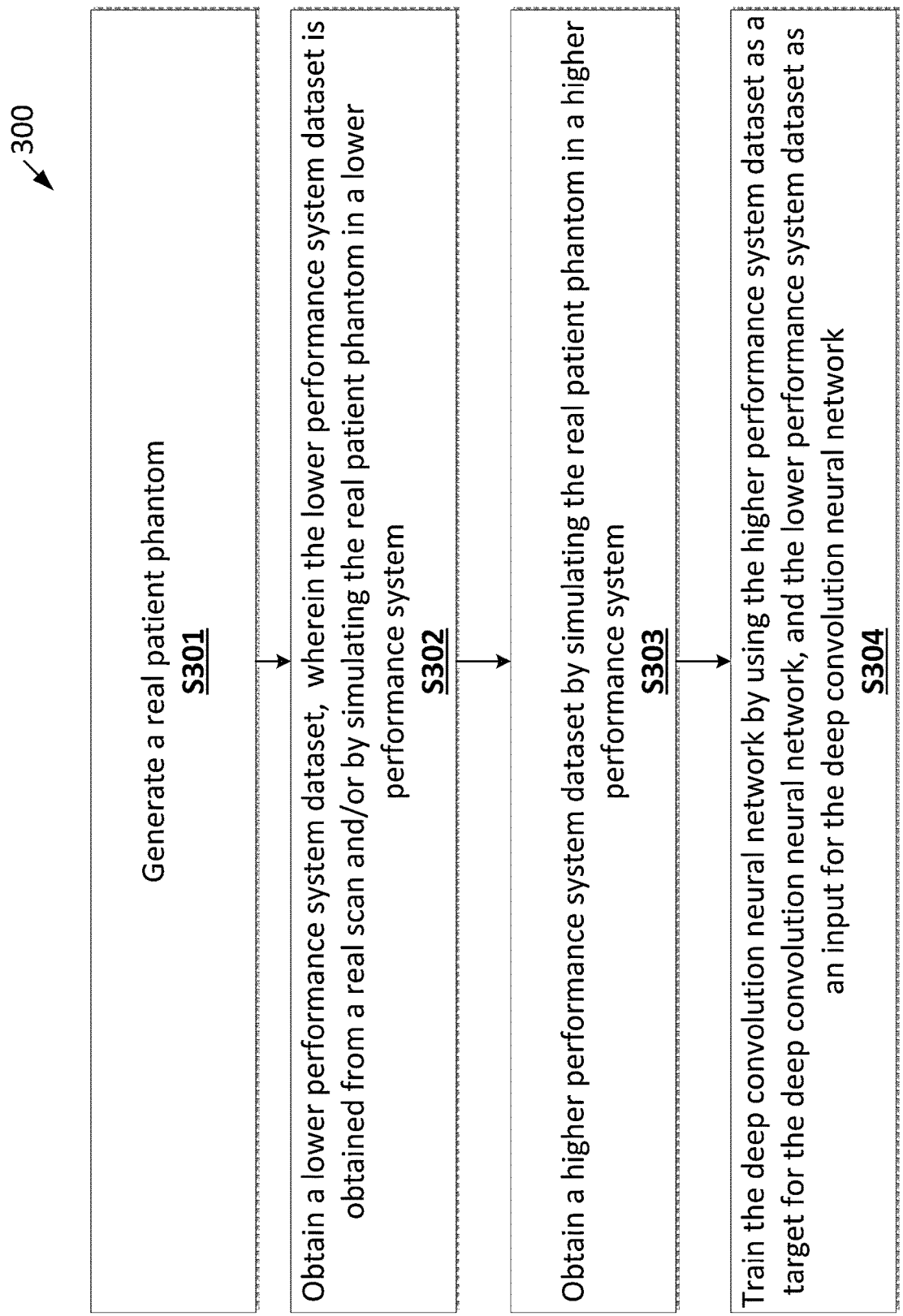
FIG. 3 is a method for training a neural network to produce a trained neural network, according to one exemplary aspect.

FIG. 3 describes one method 300 for training the deep convolution neural network that can be used in method 200. In S301, generate a RPP (i.e. third radiation data). The RPP restores existing, low quality radiation data (i.e. fourth radiation data) through reconstruction or a combination of post-reconstruction techniques, including denoising and partial volume correction. The goal is to generate a low noise, piece-wise smooth image with sharp organ/lesion boundaries, while maintaining the radiotracer distribution. This can be achieved by multiple solutions, including but not limited to: (1) penalized image reconstruction incorporating high resolution anatomical image; (2) image domain denoising incorporating high resolution anatomical image; (3) sinogram domain denoising followed by image domain partial volume correction; (4) image domain denoising followed by image domain partial volume correction; (5) penalized image reconstruction followed by image domain partial volume correction; (6) image domain denoising using a neural network that incorporates anatomical information.

Exemplary implementation of penalized image reconstruction incorporating high resolution anatomical image can be found in (1) [Chan 2009]: C. Chan, R. Fulton, D. Feng, and S. Meikle, "Regularized image reconstruction with an anatomically adaptive prior for positron emission tomography," Phys. Med. Biol., vol. 54, pp. 7379-7400, 2009. Exemplary implementation of image domain denoising incorporating high resolution anatomical image can be found in (2) [Chan 2014]: C. Chan, R. Fulton, R. Barnett, D. D. Feng, and S. Meikle, "Postreconstruction Nonlocal Means Filtering of Whole-Body PET With an Anatomical Prior," IEEE Trans. Med. Imag., vol. 33, pp. 636-650, 2014. Exemplary implementation of image domain denoising followed by image domain partial volume correction can be found in (3) [Golla 2017]: Golla, S. S. V., Lubberink, M., van Berckel, B. N. M. et al. Partial volume correction of brain PET studies using iterative deconvolution in combination with HYPR denoising. *EJNMMI Res* 7, 36 (2017). Exemplary implementation of penalized image reconstruction followed by image domain partial volume correction can be found in (4) [Chan 2016]: Chan C, Liu H, Grobshtein Y, Stacy M R, Sinusas A J, Liu C. Noise suppressed partial volume correction for cardiac SPECT/CT. *Med Phys.* 2016; 43(9):5225. doi:10.1118/1.4961391. Exemplary implementation of image domain denoising using a neural network that incorporates anatomical information can be found in (5) [Gong 2018]: Kuang Gong, Jiahui Guan, Kyungsang Kim, Xuezhu Zhang, Jaewon Yang, Youngho Seo, El Fakhri G, Jinyi Qi, Quanzheng Li. Iterative PET Image Reconstruction Using Convolutional Neural Network Representation. IEEE Trans Med Imaging. 2019 March;38(3):675-685. doi: 10.1109/TMI.2018.2869871. Epub 2018 September 12. PMID: 30222554; PMCID: PMC6472985.

As one example of generating an RPP, a non-local means method can estimate the denoised pixel $NL(x_i)$ as a weighted average of the intensity values of all pixels $x_j$ within a search window $\Omega_i$ according to the similarity of patches of pixels surrounding $x_i$ and $x_j$. In other words:

$$NL(x_i) = \sum_{j \in \Omega_i} w_{ij} x_j \quad (1)$$

$$w_{ij} = \frac{1}{Z(i)} \exp\left\{-\frac{\|x_i - x_j\|_2^2}{h^2}\right\} \quad (2)$$

where $\|x_i - x_j\|_2^2$ is a similarity between patches around pixels j and k, $\Omega_i$ is a search window centered at the current pixel i, and h is a parameter that controls the overall smoothing strength.

Furthermore, to improve PET spatial resolution, one can incorporate anatomical prior information of the same subject from either MR or CT images, such that the weight $w_{ij}$ is multiplied by a binary factor $b_{ij}$, which is determined by the similarity between pixels u_i and u_j on the anatomical CT or MR image in the same search window. In other words:

$$b_{ij} = \begin{cases} 1, & \text{if } \mu < \frac{c_i}{c_j} < \frac{1}{\mu} \\ 0, & \text{otherwise} \end{cases} \quad (3)$$

$$w_{ij} = \frac{1}{z(i)} \exp\left\{-\frac{\|x_i - x_j\|_2^2}{h^2}\right\} \cdot b_{ij} \quad (4)$$

$$NL(x_i) = \sum_{j \in N(i)} w_{ij} x_j \quad (5)$$

where μ is a parameter that controls the strength of the anatomical prior information.

For example, for μ=0.7, which means any pair of the pixels, $c_i$ and $c_j$, in the anatomical image with ratio greater than 0.7 are assumed to belong to the same or similar tissue according to their normalized intensity value. The patch centered at pixel $x_j$ in the PET image will then be used to calculate the averaging weight $w_{ij}$. If pixel $c_j$ is located in a different organ, the ratio between $c_i$ and $c_j$ will be smaller than μ, then the patch centered at pixel $c_j$ in the PET image will be excluded from the similarity measurement. The smoothing is thus penalized across organ boundaries. For generating an RPP, a large h can be selected to achieve piece-wise smooth images (smooth within organs while preserving sharp boundaries across organs).

In S302, obtain a lower performance system dataset by simulating obtaining the RPP in a lower performance system, by scanning an object in a real scan with an existing, real system (e.g. PET scanner 100), or a combination thereof. In one exemplary embodiment, the lower performance system used in the simulating can be modelled after the apparatus used to gather the first radiation data in S201 of FIG. 2, such as the PET scanner 100. According to one exemplary aspect, in simulating, the RPP can be used as a voxelized phantom in a Monte Carlo simulation (e.g. GATE), which accurately models the lower performance system's geometry, physics and stochastic nature of photon emission and detection processes to generate the lower performance system dataset.

In S303, obtain a higher performance system dataset by simulating obtaining the RPP in a higher performance system. According to one exemplary aspect, in simulating, the RPP can be used a voxelized phantom in a Monte Carlo simulation (e.g. GATE), which accurately model the higher performance system's geometry, physics and stochastic nature of photon emission and detection processes to generate the lower performance system dataset.

Figure 4A:
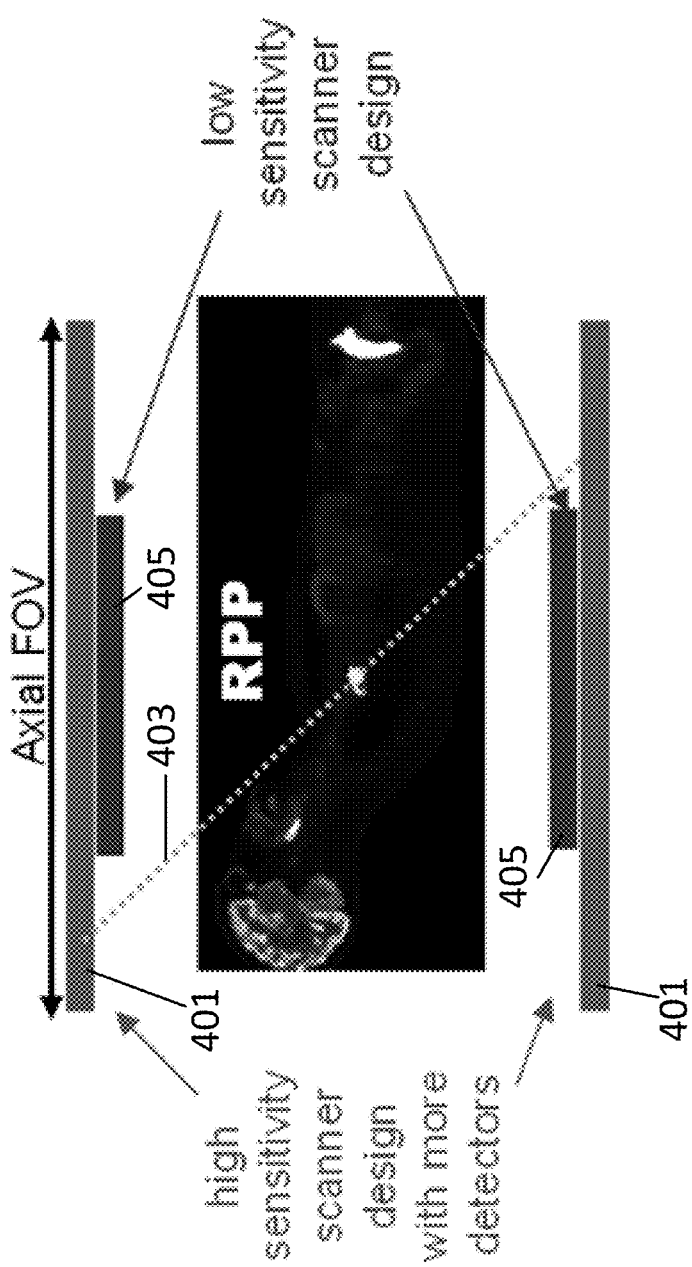
FIG. 4A illustrates a higher sensitivity scanner with a larger axial field of vision versus a lower sensitivity scanner with a smaller axial field of vision, according to one exemplary aspect.
Figure 4B:
FIG. 4B illustrates a real patient phantom (RPP) simulated in a higher sensitivity scanner with a larger axial field of vision versus an RPP simulated in a lower sensitivity scanner with a smaller axial field of vision, according to one exemplary aspect.
Figure 4B:
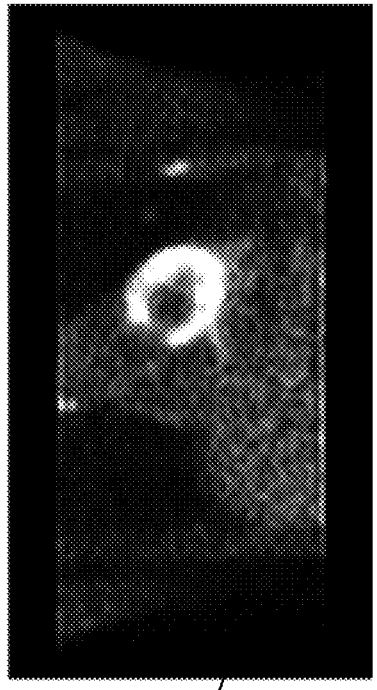

In one embodiment, the higher performance system used in simulating has a greater sensitivity than the lower performance system. This can be accomplished by the higher performance system having an increased axial field of vision. An increased axial field of vision can enable the higher performance system to collect more radiation data, thereby producing higher quality images. For example, as shown in FIG. 4A, the high sensitivity scanner 401 (system with the larger axial field of vision) can detect a line of response 403 that the low sensitivity scanner 405 (system with a smaller axial field of vision) cannot. This capability to collect more radiation data results in improved noise reduction. As illustrated in FIG. 4B, the higher performance system dataset 407 generated from the high sensitivity scanner 401 has less noise than the lower performance system dataset 409 generated from the low sensitivity scanner 405.

Figure 5:
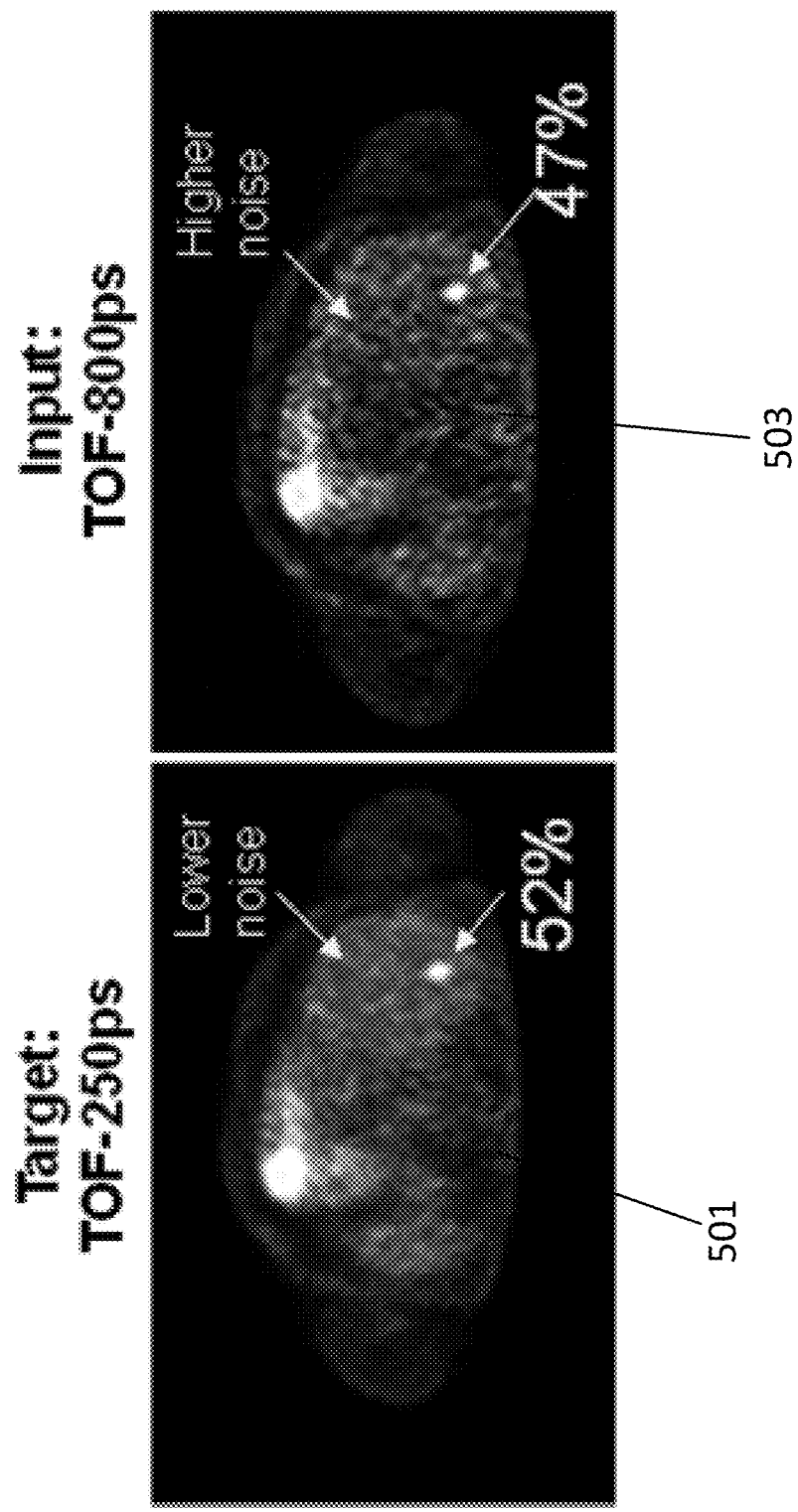
FIG. 5 illustrates an RPP simulated in a higher performance scanner with a 250 picosecond time of flight resolution versus an RPP simulated in a lower performance scanner with a 800 picosecond time of flight resolution, according to one exemplary aspect.

In one embodiment, the higher performance system used in simulating has a higher resolution TOF measurement capability than the lower performance system. For example, the higher performance system can simulate the RPP in GATE using a TOF resolution of 250 ps, whereas the lower performance system simulates the RPP in GATE using a TOF resolution of 800 ps. A lower TOF resolution can improve PET image signal-to-noise ratio. For example, as shown in FIG. 5, upon scanning the RPP in respective scanners, the higher performance system dataset 501 captured using a TOF of 250 ps had less noise than the lower performance system dataset 503 captured using a TOF of 800 ps.

In another embodiment, the higher performance system used in the simulating can have a higher intrinsic system resolution than the lower performance system. As one example, this can be accomplished by the higher performance system having smaller detector crystals than the lower performance system.

In another embodiment, the higher performance system used in the simulating can have less or no scatter (e.g. Compton scatter, background radiation within crystals), whereas the lower performance system includes more scatter.

Referencing back to FIG. 3, in S304, train the DCNN by using the higher performance system dataset obtained in S303 as a target for the DCNN, and the lower performance system dataset obtained in S302 as an input for the DCNN. The DCNN can be trained using any method known by those of ordinary skill in the art (e.g. back propagation). In one exemplary embodiment, during training, the DCNN can be optimized to minimize the radiation data difference (i.e. image quality differences) between these systems. The training can continue using multiple high/low image pairs until a stopping criteria has been met, such as a maximum number of iterations, predefined number of errors, or any other appropriate stopping criteria known by those in the art.

Figure 6:
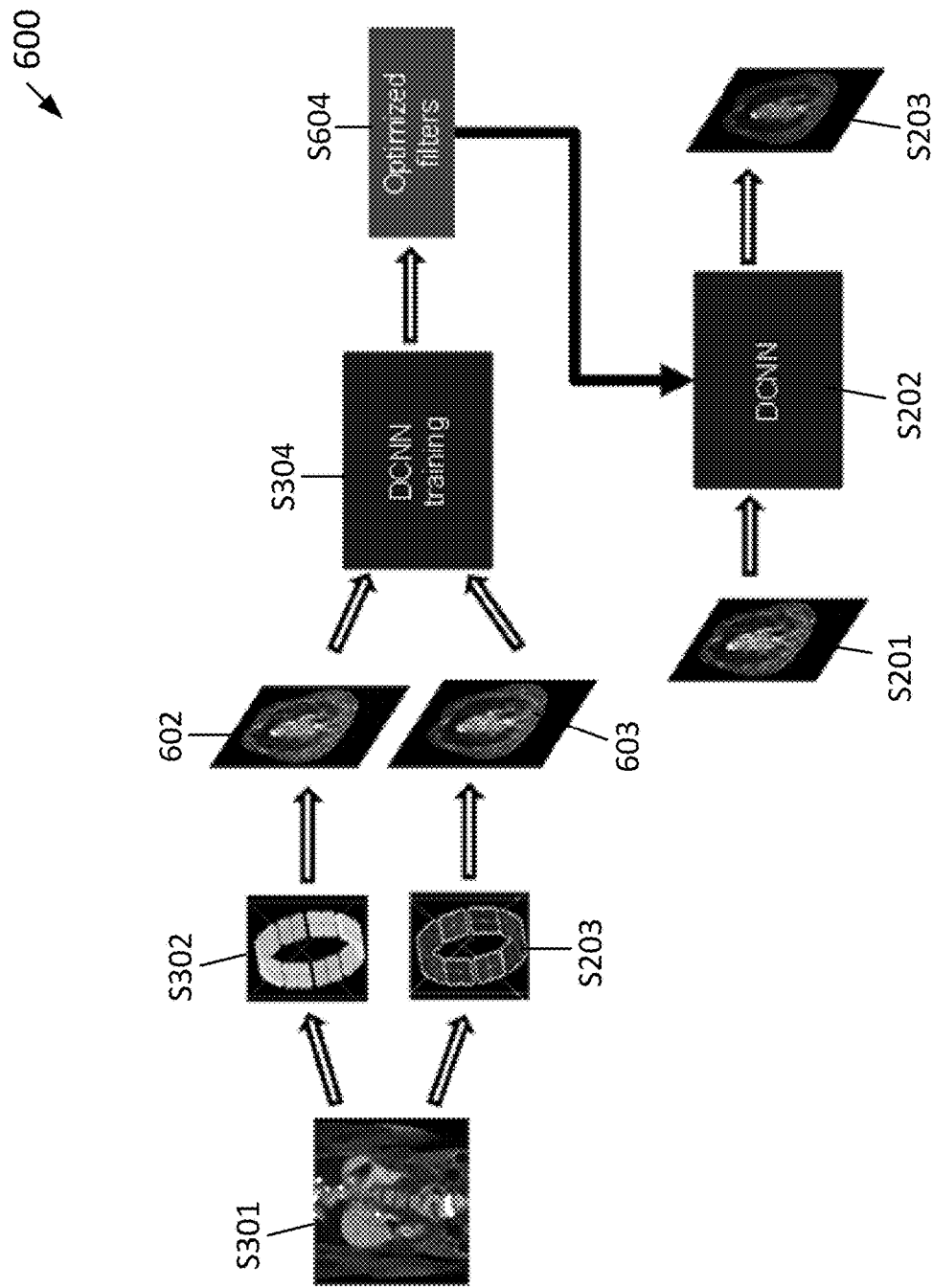
FIG. 6 is a workflow for training and using a trained neural network for inferencing, according to one exemplary aspect.

According to one exemplary embodiment, an overall workflow 600 is shown in FIG. 6. First, an RPP is generated, as discussed in S301. Then, low quality inputs 602 are generated using the RPP as a voxelized phantom in the simulated existing system, as discussed in S302. Additionally, high quality targets 603 are generated using the RPP as a voxelized phantom in the simulated high performance system, as discussed in S303. The low quality inputs 602 and high quality targets 603 are used as training data and fed into the DCNN for training, as discussed in S304.

After the DCNN training S304, the DCNN contains optimized filters. In S604, the DCNN can be optimized, which can include pruning, precision reduction, or a combination thereof. Pruning can include removing unnecessary weights in the neural network, and precision reduction can include lowering the bits that the neural network operates at.

After S604, the DCNN is trained, optimized, and ready for real-time inferencing. First, the PET scanner 100 captures real (first) radiation data of an object OBJ, as discussed in S201. According to one exemplary embodiment, this radiation data can be pre-processed (e.g. signal preconditioning, position corrections, energy corrections) and reconstructed into an image. Next, this radiation data is input into the trained DCNN, as discussed in S202. Lastly, as discussed in S203, higher quality (second) radiation data is generated and output as a high performance system data. The result is a radiation dataset (e.g. image data, sinogram data) that is generated as if it was captured by a higher performance system even though it was captured by a lower performance system.

In another embodiment, the RPP can be used to augment existing training datasets to improve the DCNN's performance. The RPP can be used to generate target images to train image restoration neural networks for dynamic, respiratory and cardiac PET acquisitions. The RPP can be used as a voxelized phantom in a Monte Carlo simulation to generate a high quality image for use as the target in DCNN training. A real study (input) and a whole-body or organ specific RPP (target) can be used as training data to produce a trained DCNN.

In another embodiment, the DCNN training can be used to refine a pre-existing DCNN, for example, using Transfer Learning. The refined DCNN can then be used for generating higher performance system datasets.

The method and system described herein can be implemented in a number of technologies but generally relate to imaging devices and processing circuitry for performing the processes described herein. In one embodiment, the processing circuitry (e.g., image processing circuitry and controller circuitry) is implemented as one of or as a combination of: an application specific integrated circuit (ASIC), a field programmable gate array (FPGA), a generic array of logic (GAL), a programmable array of logic (PAL), circuitry for allowing one-time programmability of logic gates (e.g., using fuses) or reprogrammable logic gates. Furthermore, the processing circuitry can include a computer processor and having embedded and/or external non-volatile computer readable memory (e.g., RAM, SRAM, FRAM, PROM, EPROM, and/or EEPROM) that stores computer instructions (binary executable instructions and/or interpreted computer instructions) for controlling the computer processor to perform the processes described herein. The computer processor circuitry may implement a single processor or multiprocessors, each supporting a single thread or multiple threads and each having a single core or multiple cores. In an embodiment in which neural networks are used, the processing circuitry used to train the artificial neural network need not be the same as the processing circuitry used to implement the trained artificial neural network that performs the calibration described herein. For example, processor circuitry and memory may be used to produce a trained artificial neural network (e.g., as defined by its interconnections and weights), and an FPGA may be used to implement the trained artificial neural network. Moreover, the training and use of a trained artificial neural network may use a serial implementation or a parallel implementation for increased performance (e.g., by implementing the trained neural network on a parallel processor architecture such as a graphics processor architecture). The generation of an RPP or GATE Monte Carlo simulations can also run on serial or parallel threads.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

Embodiments of the present disclosure may also be as set forth in the following parentheticals.

(1) A medical image processing apparatus comprising: processing circuitry configured to, obtain first radiation data from the medical image processing apparatus; and generate second radiation data by inputting the first radiation data into a trained neural network, wherein the trained neural network is a neural network trained by obtaining a higher performance system dataset by simulating obtaining by a higher performance system third radiation data, obtaining a lower performance system dataset, and training the neural network by using the higher performance system dataset as a target for the neural network, and the lower performance system dataset as an input for the neural network.

(2) The apparatus of (1), wherein the third radiation data is generated by reconstructing fourth radiation data using at least one of denoising and partial volume correction techniques.

(3) The apparatus of any (1) to (2), wherein the higher performance system has a higher resolution time of flight measurement capability than the lower performance system.

(4) The apparatus of any (1) to (3), wherein the higher performance system has a greater sensitivity than the lower performance system.

(5) The apparatus of any (1) to (4), wherein the higher performance system has smaller detector crystals than the lower performance system.

(6) The apparatus of any (1) to (5), wherein the higher performance system has less scattering than the lower performance system.

(7) The apparatus of any (1) to (6), wherein the first, second, third, and fourth radiation data are at least one of PET data and CT data.

(8) The apparatus of any (1) to (7), wherein the first, second, third, and fourth radiation data are gated PET data.

(9) The apparatus of any (1) to (8), wherein the lower performance system dataset is obtained from at least one of (a) a real scan by the medical image processing apparatus and (b) simulating obtaining by a lower performance system the third radiation data.

(10) The apparatus of any (1) to (9), wherein the neural network is a deep convolution neural network.

(11) A method comprising: obtaining first radiation data from a medical image processing apparatus; and generating second radiation data by inputting the first radiation data into a trained neural network, wherein the trained neural network is a neural network trained by obtaining a higher performance system dataset by simulating obtaining by a higher performance system third radiation data, obtaining a lower performance system dataset, and training the neural network by using the higher performance system dataset as a target for the neural network, and the lower performance system dataset as an input for the neural network.

(12) The method of (11), wherein the third radiation data is generated by reconstructing fourth radiation data using at least one of denoising and partial volume correction techniques.

(13) The method of any (11) to (12) wherein the higher performance system has a higher resolution time of flight measurement capability than the lower performance system.

(14) The method of any (11) to (13), wherein the higher performance system has a greater sensitivity than the lower performance system.

(15) The method of any (11) to (14), wherein the higher performance system has smaller detector crystals than the lower performance system.

(16) The method of any (11) to (15), wherein the higher performance system has less scattering than the lower performance system.

(17) The method of any (11) to (16), wherein the first, second, third, and fourth radiation data are at least one of PET data and CT data.

(18) The method of any (11) to (17), wherein the lower performance system dataset is obtained from at least one of (a) a real scan by the medical image processing apparatus and (b) simulating obtaining by a lower performance system the third radiation data.

(19) The method of any (11) to (18), wherein the neural network is a deep convolution neural network.

(20) A non-transitory computer-readable storage medium storing computer-readable instructions that, when executed by a computer, cause the computer to perform a method comprising: receiving first radiation data from a medical image processing apparatus; and generating second radiation data by inputting the first radiation data into a trained neural network, wherein the trained neural network is a neural network trained by obtaining a higher performance system dataset by simulating obtaining by a higher performance system third radiation data, obtaining a lower performance system dataset, and training the neural network by using the higher performance system dataset as a target for the neural network, and the lower performance system dataset as an input for the neural network.

What is claimed is:

1. A medical image processing apparatus, comprising:
processing circuitry configured to
obtain first radiation data from the medical image processing apparatus; and
generate second radiation data by inputting the first radiation data into a trained neural network, wherein the trained neural network is a neural network trained by
reconstructing an image from radiation data obtained from imaging an object;
generating a digital real-patient phantom (RPP) using the reconstructed image;
obtaining a higher performance system dataset by generating, via a first computer of a simulated higher performance system, third radiation data, the RPP being used as a voxelized phantom within the first computer simulation of the higher performance system to generate the third radiation data,
obtaining a lower performance system dataset by generating, via a second computer of a simulated lower performance system, fourth radiation data, the RPP being used as a voxelized phantom within the second computer simulation of the lower performance system to generate the fourth radiation data, and
training the neural network by using the obtained higher performance system dataset as a target for the neural network, and the obtained lower performance system dataset as an input to the neural network.

2. The apparatus of claim 1, wherein the step of generating the RPP further comprises generating the RPP using at least one of denoising and partial volume correction techniques on the reconstructed image.

3. The apparatus of claim 1, wherein the higher performance system has a higher resolution time-of-flight measurement capability than the lower performance system.

4. The apparatus of claim 1, wherein the higher performance system has a greater sensitivity than the lower performance system.

5. The apparatus of claim 1, wherein the higher performance system has smaller detector crystals than the lower performance system.

6. The apparatus of claim 1, wherein the higher performance system has less scattering than the lower performance system.

7. The apparatus of claim 2, wherein the first, second, third, and fourth radiation data are at least one of PET data and CT data.

8. The apparatus of claim 2, wherein the first, second, third, and fourth radiation data are gated PET data.

9. The apparatus of claim 1, wherein the neural network is a deep convolution neural network.

10. A method, comprising:
obtaining first radiation data from a medical image processing apparatus; and
generating second radiation data by inputting the first radiation data into a trained neural network, wherein the trained neural network is a neural network trained by
reconstructing an image from radiation data obtained from imaging an object;
generating a digital real-patient phantom (RPP) using the reconstructed image;

obtaining a higher performance system dataset by generating, via a first computer simulation of a higher performance system, third radiation data, the RPP being used as a voxelized phantom within the first computer simulation of the higher performance system to generate the third radiation data, obtaining a lower performance system dataset by generating, via a second computer simulation of a lower performance system, fourth radiation data, the RPP being used as a voxelized phantom within the second computer simulation of the lower performance system to generate the fourth radiation data, and training the neural network by using the obtained higher performance system dataset as a target for the neural network, and the obtained lower performance system dataset as an input to the neural network.

11. The method of claim 10, wherein the step of generating the RPP further comprises generating the RPP using at least one of denoising and partial volume correction techniques on the reconstructed image.

12. The method of claim 10, wherein the higher performance system has a higher resolution time-of-flight measurement capability than the lower performance system.

13. The method of claim 10, wherein the higher performance system has a greater sensitivity than the lower performance system.

14. The method of claim 10, wherein the higher performance system has smaller detector crystals than the lower performance system.

15. The method of claim 10, wherein the higher performance system has less scattering than the lower performance system.

16. The method of claim 11, wherein the first, second, third, and fourth radiation data are at least one of PET data and CT data.

17. The method of claim 10, wherein the neural network is a deep convolution neural network.

18. A non-transitory computer-readable storage medium storing computer-readable instructions that, when executed by a computer, cause the computer to perform a method comprising:

receiving first radiation data from a medical image processing apparatus; and generating second radiation data by inputting the first radiation data into a trained neural network, wherein the trained neural network is a neural network trained by reconstructing an image from radiation data obtained from imaging an object;

generating a digital real-patient phantom (RPP) using the reconstructed image;

obtaining a higher performance system dataset by generating, via a first computer simulation of a higher performance system, third radiation data, the RPP being used as a voxelized phantom within the first computer simulation of the higher performance system to generate the third radiation data, obtaining a lower performance system dataset by generating, via a second computer simulation of a lower performance system, fourth radiation data, the RPP being used as a voxelized phantom within the second computer simulation of the lower performance system to generate the fourth radiation data, and training the neural network by using the obtained higher performance system dataset as a target for the neural network, and the obtained lower performance system dataset as an input to the neural network.

* * * * *